United States Patent
Badiei et al.

(10) Patent No.: US 8,884,217 B2
(45) Date of Patent: *Nov. 11, 2014

(54) MULTIMODE CELLS AND METHODS OF USING THEM

(71) Applicant: Perkinelmer Health Sciences, Inc., Waltham, MA (US)

(72) Inventors: Hamid Badiei, Woodbridge (CA); Kaveh Kahen, Maple (CA)

(73) Assignee: Perkinelmer Health Sciences, Inc., Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/854,458

(22) Filed: Apr. 1, 2013

(65) Prior Publication Data

US 2013/0284917 A1    Oct. 31, 2013

Related U.S. Application Data

(63) Continuation of application No. 13/277,594, filed on Oct. 20, 2011, now Pat. No. 8,426,804, which is a continuation of application No. PCT/US2011/026463, filed on Feb. 28, 2011.

(60) Provisional application No. 61/308,461, filed on Feb. 26, 2010.

(51) Int. Cl.
  *H01J 49/02* (2006.01)
  *H01J 49/24* (2006.01)
  *G01N 30/16* (2006.01)
  *G01N 30/24* (2006.01)
  *G01N 30/60* (2006.01)

(52) U.S. Cl.
  CPC ............. *H01J 49/24* (2013.01); *G01N 30/24* (2013.01); *G01N 30/6026* (2013.01); *G01N 30/16* (2013.01)
  USPC ........................................................ 250/281

(58) Field of Classification Search
  CPC ..................... H01J 49/004; H01J 49/005
  USPC .................................................. 250/281–300
  See application file for complete search history.

(56) References Cited

U.S. PATENT DOCUMENTS

| 5,345,079 A | 9/1994 | French |
| 5,381,008 A | 1/1995 | Tanner |

(Continued)

FOREIGN PATENT DOCUMENTS

| WO | 9722233 | 6/1997 |
| WO | 9829896 | 7/1998 |

(Continued)

OTHER PUBLICATIONS

ISR/WO for PCT/US11/26463 mailed on Jul. 27, 2011.

(Continued)

*Primary Examiner* — Jack Berman
(74) *Attorney, Agent, or Firm* — Rhodes IP PLC; Christopher R Rhodes

(57) ABSTRACT

A mass spectrometer system is provided that is configurable for operation in both a Kinetic Energy Discrimination (KED) and Dynamic Reaction Cell (DRC). A pressurized or collision cell included in the mass spectrometer encloses a quadrupole and is coupled to a source of both inert and reactive gas. To operate in the KED mode, the collision cell can be filled with a quantity of the inert gas and an energy barrier formed between the collision cell and a downstream mass analyzer. Interferer ions collided with the inert gas can lose on average more energy relative to analyte ions of the same mass to charge ratio and can thus be trapped by the energy barrier in greater proportions. To operate instead in the DRC mode, the collision cell can be filled with a quantity of gas that is reactive with the interferer ions only. Mass filtering of the product ions can then transmit proportionally more of the analyte ions to the downstream mass analyzer. A mode controller coordinates the two modes of operation.

19 Claims, 2 Drawing Sheets

(56) References Cited

U.S. PATENT DOCUMENTS

| | | |
|---|---|---|
| 5,565,679 A | 10/1996 | Tanner |
| 5,652,427 A | 7/1997 | Whitehouse et al. |
| 5,684,581 A | 11/1997 | French |
| 5,969,352 A | 10/1999 | French |
| 6,140,638 A | 10/2000 | Tanner |
| 6,627,877 B1 | 9/2003 | Davis |
| 6,627,912 B2 | 9/2003 | Bandura |
| 6,875,618 B2 | 4/2005 | Bandura |
| 6,914,241 B2 | 7/2005 | Giles |
| 7,135,296 B2 | 11/2006 | Baranov |
| 7,145,137 B2 | 12/2006 | Montaser |
| RE39,627 E | 5/2007 | Tanner |
| 7,317,186 B2 | 1/2008 | Montaser |
| 7,479,630 B2 | 1/2009 | Bandura |
| 7,483,767 B2 | 1/2009 | Montaser |
| 7,700,295 B2 | 4/2010 | Baranov |
| 7,767,407 B2 | 8/2010 | Baranov |
| 7,804,064 B2 | 9/2010 | Montaser |
| 8,426,804 B2 * | 4/2013 | Badiei et al. ............. 250/281 |
| 2005/0224709 A1 | 10/2005 | Montaser |
| 2005/0230617 A1 | 10/2005 | Montaser |
| 2006/0087651 A1 | 4/2006 | Montaser |
| 2007/0299561 A1 | 12/2007 | Montaser |
| 2009/0134326 A1 | 5/2009 | Bandura |
| 2009/0179161 A1 | 7/2009 | Ward |
| 2011/0210241 A1 | 9/2011 | Badiei |
| 2011/0253888 A1 | 10/2011 | Badiei |

FOREIGN PATENT DOCUMENTS

| | | |
|---|---|---|
| WO | 02054075 | 7/2002 |
| WO | 03009332 | 1/2003 |
| WO | 2005003767 | 1/2005 |
| WO | 2005093784 | 10/2005 |

OTHER PUBLICATIONS

Bandura et al. Anal Chem., vol. 81, No. 16, pp. 6813-6822, 2009.
Sturgeon et al. J. Anal. St. Spectrom., 16, pp. 607-616, 2000.
Praphairaksit et al. Anal. Chem., vol. 72, No. 11, Jun. 1, 2000.
Tanner et al. Appl. Spectroscopy, vol. 48, No. 11, 1994.

* cited by examiner

US 8,884,217 B2

MULTIMODE CELLS AND METHODS OF USING THEM

PRIORITY APPLICATION

This application claims priority to, and the benefit of, U.S. Provisional Application No. 61/308,676 filed on Feb. 26, 2010, the entire disclosure of which is hereby incorporated herein by reference for all purposes.

FIELD

Embodiments of the present invention relate generally to a mass spectrometer system, and method of operating the same, and more particularly to a method of operating the mass spectrometer system in a dual-mode to suppress unwanted ions.

INTRODUCTION

Mass spectrometry (MS) is an analytical technique for determining the elemental composition of unknown sample substances that has both quantitative and qualitative applications. For example, MS can be useful for identifying unknown compounds, determining the isotopic composition of elements in a molecule, and determining the structure of a particular compound by observing its fragmentation, as well as for quantifying the amount of a particular compound in the sample. Mass spectrometry can operate by ionizing the test sample using one of many different available methods to form a stream of positively charged particles, i.e. an ion stream. The ion stream can then be subjected to mass differentiation (in time or space) to separate different particle populations in the ion stream according to mass-to-charge (m/z) ratio. A downstream mass analyzer can then detect the intensities of the mass-differentiated particle populations in order to compute analytical data of interest, e.g. the relative concentrations of the different particle's populations, mass-to-charge ratios of product or fragment ions, but also other potentially useful analytical data.

In mass spectrometry, ions of interest ("analyte ions") can coexist in the ion stream with other unwanted ion populations ("interferer ions") that have substantially the same nominal m/z ratio as the analyte ions. In other cases, the m/z ratio of the interferer ions, through not identical, will be close enough to the m/z ratio of the analyte ions that it falls within the resolution of the mass analyzer, thereby making the mass analyzer unable to distinguish the two types of ions. Improving the resolution of the mass analyzer is one approach to dealing with this type of interference (commonly referred to as "isobaric" or "spectral interference"). Higher resolution mass analyzers, however, tend to have slower extraction rates and higher loss of ion signals requiring more sensitive detectors. Limits on the achievable resolution may also be encountered.

Beyond spectral interferences, additional non-spectral interferences are also commonly encountered in mass spectrometry. These can derive from neutral metastable species of particles, and produce an elevated background over a range of masses (so that it is non-spectral). This elevated background adversely affects the detection limit of the instrument. Some common non-spectral interferences in the ion stream include photons, neutral particles, and gas molecules.

SUMMARY

In accordance with an aspect of embodiments of the present invention, there is described a method of operating a mass spectrometer system comprising a pressurized cell. The method comprises the steps of: a) emitting an ion stream from an ion source, the ion stream comprising a plurality of groups of ions of a plurality of different kinds, including a first group of ions of a first kind and a second group of ions of a second kind, wherein each respective group of ions comprises individual ions of i) a corresponding kind in the plurality of different kinds, and ii) energies that define a corresponding energy distribution for that respective group of ions, and wherein individual ions in the first group of ions have on average a larger collisional cross-section than individual ions in the second group of ions; b) transmitting to, and admitting the ion stream into, an entrance end of the pressurized cell, the pressurized cell being a quadrupole pressurized cell comprising a quadrupole rod set; c) during b), for each respective group of ions in the ion stream, controlling a range of the corresponding energy distribution to lie within a selected maximum range; d) supplying an RF voltage to the quadrupole rod set to form a quadrupolar field therewithin for radial confinement of ions being transmitted from the entrance end to an exit end of the pressurized cell downstream of the entrance end; e) focusing the ion stream at a location upstream of the quadrupole rod set to direct most of the ion stream within an acceptance ellipse of the quadrupole rod set; f) providing an inert gas within the pressurized cell, the inert gas being substantially non-reactive with ions of the first and second kinds, to collide with a first proportion of the first group of ions and a second proportion of the second group of ions, the first proportion being substantially greater than the second proportion, to reduce the energies of the individual ions in the first group of ions to a greater extent than in the second group of ions; and, g) providing an exit barrier at the exit end of the pressurized cell of a strength selected to prevent a larger proportion of the reduced energy ions in the first group of ions than in the second group of ions from penetrating the exit barrier.

In accordance with another aspect of embodiments of the present invention, there is described a mass spectrometer system. The mass spectrometer comprises: an ion source operable to emit an ion stream comprising a plurality of groups of ions of a plurality of different kinds, including a first group of ions of a first kind and a second group of ions of a second kind, wherein each respective group of ions comprises individual ions of i) a corresponding kind in the plurality of different kinds, and ii) energies that define a corresponding energy distribution for that respective group of ions, and wherein individual ions in the first group of ions have on average a larger collisional cross-section than individual ions in the second group of ions; a pressurized cell comprising i) an ion inlet at an entrance end of the pressurized cell for receiving the ion stream into the pressurized cell, and ii) a quadrupole rod set; a voltage source linked to the quadrupole rod set, the voltage source operable to supply an RF voltage to the quadrupole rod set to form a quadrupolar field therewithin for radial confinement of ions being transmitted from the entrance end to an exit end of the pressurized cell downstream of the entrance end, such that the pressurized cell is operable as a quadrupole pressurized cell; ion optics included at a location upstream of the quadrupole rod set to control, for each respective group of ions in the ion stream, a range of the corresponding energy distribution to lie within a selected maximum range throughout transmission of the ion stream to the pressurized cell, and further to direct most of the ion stream within an acceptance ellipse of the quadrupole rod set; an inert gas source fluidly coupled to the pressurized cell to provide a quantity of the inert gas therewithin, the inert gas being substantially non-reactive with ions of the first and second kinds, to collide with a first proportion of the first group of ions and a second proportion of the second group of ions, the first proportion being substantially greater than the second proportion, to reduce the energies of the individual ions in the first group of ions to a greater extent than in the second group of ions; and, an exit barrier formed at the exit end of the pressurized cell, the exit barrier of a strength selected to prevent a larger proportion of the reduced energy ions in the first group of ions than in the second group of ions from penetrating the exit barrier.

In accordance with another aspect, a system configured to permit switching of a cell between at least two modes comprising a collision mode and a reaction mode is provided. In certain examples, the system comprises a cell configured to receive a collision gas in a collision mode to pressurize the cell and configured to receive a reactive gas in a reaction mode to pressurize the cell. In some examples, the system can include a controller electrically coupled to the cell, the controller configured to provide a first effective voltage to the pressurized cell in the collision mode to select ions comprising an energy greater than a selected barrier energy, the controller further configured to provide a second effective voltage to the pressurized cell in the reaction mode to select ions using mass filtering.

In certain embodiments, the system can be further configured to permit switching to a vented mode. In some embodiments, the system can include a gas manifold fluidically coupled to a gas inlet of the cell. In additional embodiments, the cell comprises a quadrupole. In certain examples, the cell can include an exit member proximate to an exit aperture of the cell and electrically coupled to a voltage source, the exit member configured to direct analyte ions in the pressurized cell toward the exit aperture of the cell. In some examples, the exit member comprises a potential between −60 Volts and −18 Volts in the collision mode. In other examples, the exit member comprises a potential between −20 Volts and 0 Volts in the reaction mode. In further examples, the cell comprises an entrance member proximate to an entrance aperture of the cell and electrically coupled to the voltage source, the entrance member configured to direct analyte ions into the pressurized cell and toward the exit aperture of the cell. In some embodiments, the entrance member comprises a potential between −10 Volts and +2 Volts in the collision mode. In additional embodiments, the entrance member comprises a potential substantially the same as a potential of the exit member in the reaction mode.

In some embodiments, the cell (or the system) can be configured to switch from the collision mode to the reaction mode by exhausting the cell prior to introduction of a reactive gas into the cell. In other embodiments, the cell (or the system) can be configured to switch from the reaction mode to the collision mode by exhausting the cell prior to introduction of a collision gas into the cell.

In further embodiments, the system can include an additional cell coupled to the cell, the additional cell configured to receive a collision gas in a collision mode to pressurize the additional cell and a reactive gas in a reaction mode to pressurize the additional cell. In some examples, the collision gas used with the cell and the additional cell can be the same or can be different. In other examples, the reactive gas used with the cell and the additional cell can be the same or can be different.

In other embodiments, the controller can be configured to operate at least one of the cell and the additional cell in the reaction mode and to operate the other cell in a standard mode. In further embodiments, the controller can be configured to operate at least one of the cell and the additional cell in the collision mode and to operate the other cell in a standard mode. In some embodiments, the controller can be configured to operate at least one of the cell and the additional cell in the collision mode and to operate the other cell in the reaction mode. In further embodiments, the controller can be configured to operate both the cell and the additional cell in the collision mode. In some embodiments, the controller can be configured to operate both the cell and the additional cell in the reaction mode. In other examples, the controller can be configured to operate both the cell and the additional cell in a standard mode.

In some embodiments, the system can include axial electrodes electrically coupled to a voltage source and configured to provide an axial field to direct ions toward an exit aperture of the cell. In further embodiments, the axial field can include a field gradient between 0.1 V/cm and 0.5 V/cm. In some embodiments, the controller can be further configured to provide an offset voltage to the cell. In additional embodiments, the system can include a mass analyzer coupled to the cell comprising an offset voltage. In certain examples, the offset voltage of the mass analyzer can be more positive than the offset voltage of the cell when the cell is operated in the collision mode. In some examples, the offset voltage of the mass analyzer can be more negative than the offset voltage of the cell when the cell is operated in the reaction mode. In additional embodiments, the system can include an ionization source coupled to the pressurized cell. In some embodiments, the ionization source is an inductively coupled plasma. In some examples, the system can include a mass analyzer coupled to the cell. In further embodiments, the cell can be positioned between the inductively coupled plasma and the mass analyzer. In other embodiments, the cell can be positioned downstream from the mass analyzer.

In another aspect, a system comprising an ion source, a cell, a mass analyzer and a controller is described. In some embodiments, the cell can be coupled to the ion source and configured to operate in at least three different modes comprising a collision mode, a reaction mode and a standard mode. The three different modes each configured to select analyte ions from a plurality of ions introduced into the cell from the ion source, the cell configured to couple to the ion source at an entrance aperture to permit introduction of the plurality of ions from the ion source into the cell, the cell further comprising a gas inlet configured to receive a substantially inert gas to pressurize the cell in a collision mode and to receive a reactive gas to pressurize the cell in a reaction mode, the pressurized cell further comprising an exit aperture configured to provide the analyte ions from the cell. In further embodiments, the mass analyzer can be coupled to the cell. In additional embodiments, the controller can be electrically coupled to the cell and configured to provide the substantially inert gas to pressurize the cell in the collision mode, configured to provide the reactive gas to pressurize the cell in the reaction mode, and configured to maintain the cell under vacuum in the standard mode.

In certain embodiments, the controller can provide a voltage to the pressurized cell to select the analyte ions from the plurality of analyte and non-analyte ions introduced into the pressurized cell. In other embodiments, the pressurized cell comprises a quadrupole. In further embodiments, the voltage can be provided to the quadrupole to provide a quadrupolar field effective to confine a substantial amount of non-analyte ions in the plurality of introduced ions by colliding the non-analyte ions with the substantially inert gas in the collision mode. In additional examples, the system can include axial electrodes configured to provide an axial field to direct the analyte ions from the entrance aperture toward an exit aperture of the pressurized cell. In some examples, the axial field strength can have an axial field gradient between 0.1 V/c, and 0.5 V/cm.

In certain examples, the system can also include an exit member proximal to an exit aperture of the pressurized cell, the exit member comprising an exit potential to attract analyte ions toward the exit aperture of the pressurized cell. In other examples, the exit potential can be between about −60 Volts and −18 Volts in the collision mode. In some examples, the exit potential can be between about −20 Volts and 0 Volts in the reaction mode. In other examples, the system can include an entrance member proximal to the entrance aperture of the pressurized cell, the entrance member comprising an entrance potential more positive than the exit potential in the collision mode. In additional examples, the entrance potential can be between −10 Volts and +2 Volts. In some embodiments, the system can include an entrance member proximal to the entrance aperture of the pressurized cell, the entrance member comprising an entrance potential substantially the same as the exit potential in the reaction mode. In certain embodiments, the exit member can include a potential between −60 Volts and −18 Volts in the collision mode. In other examples, the exit member can include a potential between −20 Volts and 0 Volts in the reaction mode.

In some embodiments, the mass analyzer can be positioned between the ion source and the cell. In further embodiments, the mass analyzer can be positioned downstream from the cell. In additional embodiments, the system can include a detector coupled to the cell. In further embodiments, the ion source can be configured as an inductively coupled plasma.

In additional embodiments, the system can include an additional cell coupled to the cell, the additional cell configured to operate in at least three different modes comprising a collision mode, a reaction mode and a standard mode. In some embodiments, the additional cell can be configured to operate in a standard mode when the cell is being operated in the collision gas mode or the reaction mode.

In further embodiments, the controller is further configured to provide an offset voltage to the mass analyzer. In some examples, the controller can be configured to provide the offset voltage of the mass analyzer that is more positive than an offset voltage of the cell when the cell is operated in the collision mode and in which the controller is configured to provide the offset voltage of the mass analyzer that is more negative than the offset voltage of the cell when the cell is operated in the reaction mode.

In another aspect, a kit for facilitating operation of a mass spectrometer in at least two different modes comprising a collision mode and a reaction mode is provided. In some examples, the kit can facilitate operation of a mass spectrometer in at least two different modes comprising a collision mode, a reaction mode and a standard mode. In certain embodiments, the kit comprises a cell configured to receive a collision gas in the collision mode to pressurize the cell and configured to receive a reactive gas in the reaction mode to pressurize the cell, the cell further configured to receive an effective voltage from a controller electrically coupled to the cell to permit selection of ions from the cell in the collision mode using an energy barrier and to permit selection of ions from the cell in the reaction mode using mass filtering.

In certain examples, the kit can include a gas manifold configured to fluidically couple to the cell. In some examples, the kit can include a storage medium comprising a method to control switching between the various modes. In further examples, the kit can include a controller. In other examples, the kit can include an additional cell configured to receive a collision gas in the collision mode to pressurize the additional cell and configured to receive a reactive gas in the reaction mode to pressurize the additional cell, the additional cell further configured to receive an effective voltage from a controller electrically coupled to the additional cell to permit selection of ions from the additional cell in the collision mode using an energy barrier and to permit selection of ions from the additional cell in the reaction mode using mass filtering.

In an additional aspect, a method of facilitating operation of a mass spectrometer cell in at least two different modes comprising a collision mode and a reaction mode (and optionally a standard mode) is provided. In certain examples, the method comprises providing a controller configured to electrically couple to the cell, the controller configured to provide a first effective voltage to the cell in the collision mode to permit selection of ions comprising an energy greater than a selected barrier energy, the controller further configured to provide a second effective voltage to the cell in the reaction mode to permit selection of ions using mass filtering.

In another aspect, another method of facilitating operation of a mass spectrometer in at least two different modes comprising a collision mode and a reaction mode (and optionally a standard mode) is described. In certain examples, the method comprises providing a cell configured to receive a collision gas in the collision mode to pressurize the cell and configured to receive a reactive gas in the reaction mode to pressurize the cell, the cell further configured to receive an effective voltage from a controller electrically coupled to the cell to permit selection of ions from the cell in the collision mode using an energy barrier and to permit selection of ions from the cell in the reaction mode using mass filtering.

These and other features of the embodiments as will be apparent are set forth and described herein.

BRIEF DESCRIPTION OF THE DRAWINGS

A detailed description of various embodiments is provided herein below with reference, by way of example, to the following drawings.

FIG. 2b, in a rear cross-sectional view, illustrates the set of auxiliary electrodes shown in FIG. 2a.

Figure 1:
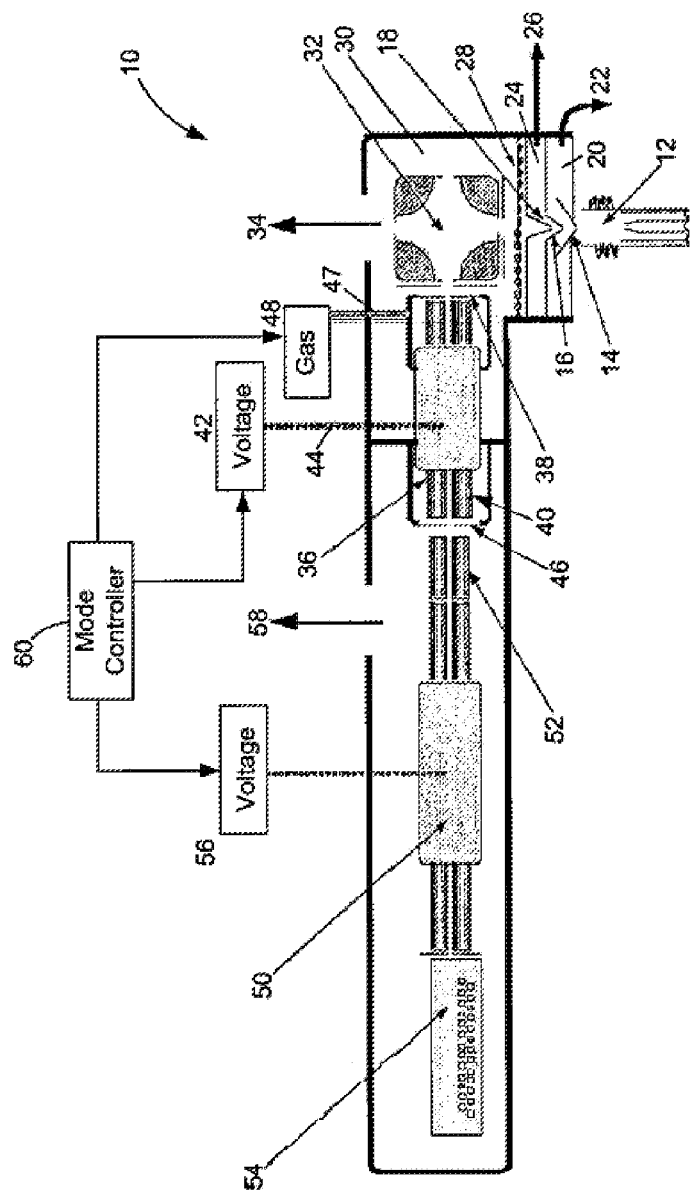
FIG. 1, in a schematic diagram, illustrates a mass spectrometer system, in accordance with aspects of embodiments of the present invention, which can be used in inductively coupled plasma MS to suppress unwanted ions.

It will be understood that the drawings are exemplary only and that any reference to them is done for the purpose of illustration only, and is not intended to limit the scope of the embodiments described herein below in any way. For convenience, reference numerals may also be repeated (with or without an offset) throughout the figures to indicate analogous components or features.

DETAILED DESCRIPTION OF EMBODIMENTS

It will be appreciated that for clarity, the following discussion will include specific details relating to various aspects of embodiments of the invention, but may also omit other details wherever convenient or appropriate to do so. For example, discussion of like or analogous features in alternative embodiments may be somewhat abbreviated. Well-known ideas or concepts may also for brevity not be discussed in any great detail. The skilled person will recognize that implementing embodiments of the invention may not require certain of the specifically described details in every case, which are included herein only to provide a thorough understanding of the embodiments. Similarly it will become apparent that the described embodiments may be susceptible to slight alteration or variation according to common general knowledge without departing from the scope of the disclosure. The following detailed description of embodiments is not to be regarded as limiting the scope of the present invention in any manner.

Certain mass spectrometry applications, for example those involving analysis of metals and other inorganic analytes, can be advantageously carried out using an inductively coupled plasma (ICP) ion source in the mass spectrometer, due to the relatively high ion sensitivities that can be achieved in ICP-MS. To illustrate, ion concentrations below one part per billion are achievable with ICP ion sources. In an inductively coupled plasma ion source, the end of a torch consisting of three concentric tubes, typically quartz, can be placed into an induction coil supplied with a radio-frequency electric current. A flow of argon gas can then be introduced between the two outermost tubes of the torch, where the argon atoms can interact with the radio-frequency magnetic field of the induction coil to free electrons from the argon atoms. This action can produce a very high temperature (perhaps 10,000K) plasma comprising mostly of argon atoms with a small fraction of argon ions and free electrons. The analyte sample can then be passed through the argon plasma, for example as a nebulized mist of liquid. Droplets of the nebulized sample can evaporate, with any solids dissolved in the liquid being broken down into atoms and, due to the extremely high temperatures in the plasma, stripped of their most loosely-bound electron to form a singly charged ion.

The ion stream generated by an ICP ion source therefore can, in addition to the analyte ions of interest, often contain a large concentration of argon and argon based spectral interference ions. Some of the more common spectral interferences include $Ar^+$, $ArO^+$, $Ar_2^+$, $ArCl^+$, $ArH^+$, and $MAr^+$ (where M denotes the matrix metal in which the sample was suspended for ionization), but also may include other spectral interferences such as $ClO^+$, $MO^+$, and the like. It will be appreciated that other types of ion sources, including glow discharge and electrospray ion sources, may also produce non-negligible concentrations of spectral interferences. It will further be appreciated that spectral interferences may be generated from other sources in MS, for example during ion extraction from the source (e.g. due to cooling of the plasma once it is subjected to vacuum pressures outside of the ICP, or perhaps due to interactions with the sampler or skimmer orifices). The momentum boundaries existing at the edges of the sampler or skimmer represent another possible source of spectral interferences.

Aside from using high-resolution mass analyzers to distinguish between analyte and interferer ions, another way of mitigating the effects of spectral interferences in the ion stream is to selectively eliminate the interferer ions upstream of the mass analysis stage. According to one approach, the ion stream can be passed through a cell, sometimes referred to as a dynamic reaction cell (DRC), which can be filled with a selected gas that is reactive with the unwanted interferer ions, while remaining more or less inert toward the analyte ions. As the ion stream collides with the reactive gas in the DRC, the interferer ions can form product ions that no longer have substantially the same or similar m/z ratio as the analyte ions. If the m/z ratio of the product ion substantially differs from that of the analyte, then conventional mass filtering can then be applied to the cell to eliminate the product interferer ions without significant disruption of the flow of analyte ions. In other words, the ion stream can be subjected to a band pass mass filter to transmit only the analyte ions to the mass analysis stage in significant proportions. Use of a DRC to eliminate interferer ions is described more fully in U.S. Pat. Nos. 6,140,638 and 6,627,912, the entire contents of which are incorporated herein by reference.

In general, DRC can provide extremely low detection limits, perhaps even on the order of parts or subparts per trillion depending on the analyte of interest. At the same isotope, certain limitations or constraints are also imposed upon DRC. For one thing, because the reactive gas must be reactive only with the interferer ion and not with the analyte, DRC is sensitive to the analyte ion of interest. Different reactive gases may need to be employed for different analytes. In other cases, there may be no known suitable reactive gas for a particular analyte. In general, it may not be possible to use a single reactive gas to address all spectral interferences.

Another potential constraint is imposed on DRC in the form of the type of cell that can be used. As will be discussed more fully below, radial confinement of ions is provided within the cell by forming a radial RF field within an elongated rod set. Confinement fields of this nature can, in general, be of different orders, but are commonly either a quadrupolar field, or else some higher order field, such as a hexapolar or octopolar field. However, DRC may be restricted to use of quadrupolar radial confinement fields if mass filtering is to be applied in the collision cell to eliminate the product interferer ions. As is known, application of small dc voltages to a quadrupole rod set, in conjunction with the applied quadrupolar RF, can destabilize ions of m/z ratios falling outside of a narrow, tunable range, thereby creating a form of mass filter for ions. Comparable techniques for other higher order poles may not be as effective as with the quadrupole rod set. Thus, at least practically speaking, DRC can be confined to a cell with a quadrupolar field.

According to another approach, which is sometimes referred to as kinetic energy discrimination (KED), the ion stream can be collided inside the collision cell with a substantially inert gas. Both the analyte and interferer ions can be collided with the inert gas causing an average loss of kinetic energy in the ions. The amount of kinetic energy lost due to the collisions can in general be related to the collisonal cross-section of the ions, which can be related to the elemental composition of the ion. Polyatomic ions (also known as molecular ions) composed of two or more bonded atoms tend to have a larger collisional cross-section than do monatomic ions, which are composed only of a single charged atom. This is so on account of the atomic spacing between the two or more bonded atoms in the polyatomic ion. Consequently, the inert gas can collide preferentially with the polyatomic atoms to cause on average a greater loss of kinetic energy than will be seen in monatomic atoms of the same m/z ratio. A suitable energy barrier established at the downstream end of the collision cell can then trap a significant portion of the polyatomic interferer and prevent transmission to the downstream mass analyzer.

Relative to DRC, KED can have the benefit of being generally more versatile and simpler to operate, in so far as the choice of inert gas does not substantially depend on the particular interferer and/or analyte ions of interest. A single inert gas, which is often helium, can be effective to remove many different polyatomic interferences of different m/z ratios, so long as the relative collisional cross-sections of the interferer and analyte ions are as described above. At the same time, certain drawbacks may be associated with KED. In particular, KED can have lower ion sensitivity than DRC because some of the reduced energy analyte ions will be trapped, along with the interferer ions, and prevented from reaching the mass analysis state. The same low levels of ions (e.g. parts and subparts per trillion) can therefore not be detected using KED. For example, detection limits can be 10 to 1000 times worse using KED relative to DRC.

To an extent, KED can also be limited in the range of radial confinement fields that can be used within the collision cell. Collisions with the inert gas cause a radial scattering of ions within the rod set. Higher order confinement fields, including hexapolar and octopolar fields, may be preferred because they can provide deeper radial potential wells than quadrupolar fields and therefore may provide better radial confinement. Quadrupolar fields are not strictly required for KED because, unlike in DRC, a mass filter is not usually utilized to discriminate against product interferer ions. In KED, the downstream energy barrier discriminates against the interferer ions in terms of their average kinetic energies relative to that of the analyte ions. Use of the available higher order poles also tends to ease requirements on the quality of ion stream, such as width of the beam and energy distributions of the respective ion populations in the beam, which in turn can ease requirements on other ion optical elements in the mass spectrometer and provide more versatility overall.

Embodiments of the present invention provide a mass spectrometer system, and method of operating the same, that is configurable for both DRC and KED modes of operation to suppress unwanted interferer ions. By controlling the ion source and other ion optical elements located upstream of the collision cell, as well as by controlling downstream components such as the mass analyzer to establish a suitable energy barrier, a quadrupole collision cell can be rendered operable for KED. Thus, a single collision cell in the mass spectrometer system can operate in both the DRC and KED modes. A mode controller coupled to the mass spectrometer can control gas and voltage sources linked to the collision cell and downstream mass analyzer to enable selectable, alternate operation of the mass spectrometer in the two described modes. Thus, in a single mass spectrometer system, the relative advantages of each type of operation can be realized, and the relative disadvantages of each avoided.

Referring initially to FIG. 1, there is illustrated a mass spectrometer system 10, in accordance with aspects of embodiments of the present invention, which can be used in ICP-MS to suppress unwanted ions. The mass spectrometer system 10 can comprise ion source 12, which can be an ICP ion source, but can also be some other type of ion source that generates substantial spectral interferences, including various known inorganic spectral interferences. Ion source 12, for example, can vaporize the analyte sample in a plasma torch to generate ions. Once emitted from the ion source 12, ions can be extracted into an ion stream by passing successively through apertures in sampler plate 14 and skimmer 16. The ion extraction provided by the sampler plate 14 and skimmer 16 can result in a narrow and highly focused ion stream. The skimmer 16 can be housed in a vacuum chamber 20 evacuated by mechanical pump 22 to an atmospheric pressure of about 3 torr, for example. In some embodiments, upon passing through the skimmer 16, the ions can enter into a second vacuum chamber 24 housing secondary skimmer 18. A second mechanical pump 26 can evacuate the second vacuum chamber 24 to a lower atmospheric pressure than the vacuum chamber 20. For example, the second vacuum, chamber can be maintained at or about 1 to 100 millitorr.

If the ion source 12 is an inductively coupled plasma source, then the ion stream passing through the skimmers 16 and 18 can suffer from spectral interferences. That is, the ion stream can be made up of populations of different kinds of ions, including one or more types of analyte ions that were ionized from the test sample. However, the ion stream may also contain populations of one or more types of interferer ions that were unavoidably introduced into the ion stream during ionization in the ICP. As described above, for inductively coupled plasma sources, which subject the test sample to very high temperature plasmas of argon typically, the above-listed inorganic spectral interferences (i.e. $Ar^+$, $ArO^+$, $Ar_2^+$, $ArCl^+$, $ArH^+$, and $MAr^+$) may be especially present in the ion stream. Of course, the skilled person would appreciate that the list is not limiting, in that other types or sources of spectral interferences may be present in the ion stream. The types of interferer ions may depend on the type of ion source 12 included in the mass spectrometer 10 and the selected analyte ion kind. Moreover, as described above, other non-spectral interferences may also be present in the ion stream, including photons of light, neutral particles and other gas molecules.

Each population (or group) of ions in the ion stream can comprise individual ions of like kind that make up the respective population. The various different populations of ions of different kinds can, together with other potential interferences, make up the ion stream. Each particular kind of ion present in the ion stream will have a corresponding m/z ratio, though it will not necessarily be unique within the ion stream as the interferer type ions may have the same or similar m/z ratio as the analyte ions. For example, the ion stream could comprise a population of $^{56}Fe^+$ analyte ions, together with a population of $^{40}Ar^{16}O^+$ interferer ions generated by the ICP. Each of these two ion types have m/z ratios of 56. As another non-limiting example, the analyte ion kind could be $^{80}Se^+$, in which case $^{40}Ar_2^+$ would constitute an interferer ion kind, each of m/z 80.

In some embodiments, the interferer ion kind can be a polyatomic kind of ion. For example, $^{40}Ar^{16}O^+$ and $^{40}Ar_2^+$ ions would be two examples of polyatomic interferer ions. The analyte ion kind can be, on the other hand, a monatomic kind of ion comprising only a single ionized atom. In the above example, $^{56}Fe^+$ and $^{80}Se^+$ ions would be two corresponding examples of monatomic analyte ions. Because the interferer type ions can be of the polyatomic kind and the analyte ions of the monatomic kind, in some embodiments, the interferer type ions can also have a larger average collisional cross-section than the analyte ions.

The respective ion populations in the ion stream emitted from the ion source 12 can also define corresponding energy distributions with respect to the energies of the individual ions making up the populations. In other words, each individual ion in a respective population can be emitted from the ion source 12 having a certain kinetic energy. The individual ion energies taken over the ion population can provide an energy distribution for that population. These energy distributions can be defined in any number of ways, for example, in terms of a mean ion energy and a suitable metric providing a measure of the energy deviation from the mean ion energy. One suitable metric can be the range of the energy distribution measured at full-width at half-max (FWHM).

When the ion stream is emitted from the ion source 12, each population of ions in the stream can have respective initial energy distributions defined, in part, by corresponding initial ranges. Of course, these initial energy distributions need not be preserved as the ion stream is transmitted from the ion source 12 to downstream components included in the mass spectrometer 10. Some energy separation in the ion populations can be expected, for example due to collisions with other particles, field interactions, and the like. It may be convenient to describe the ion stream in terms of the respective energy distributions of its constituent ion populations at different locations throughout the mass spectrometer 10. In some embodiments, each ion population has substantially the same initial range of energy distributions when emitted from the ion source 12.

In some embodiments, ions passing through the supplemental skimmer 18 can be transmitted across interface gate 28 into a third vacuum chamber 30 enclosing an ion deflector 32, such as the quadrupole ion deflector seen in FIG. 1. The atmospheric pressure in the third vacuum chamber 30 can, by means of mechanical pump 34, be maintained at even lower levels than the second vacuum chamber 24. The ion stream encountering the ion deflector 32 along an entrance trajectory can be deflected through a deflection angle, such that the ion stream exits from the ion deflector 32 along an exit trajectory that is different from the entrance trajectory for processing in additional downstream mass analytical components.

As seen in FIG. 1, the ion deflector 32 can be configured as a quadrupole ion deflector, comprising a quadrupole rod set whose longitudinal axis extends in a direction that is approximately normal to entrance and exit trajectories of the ion stream (being the direction which is normal to the plane of FIG. 1). The quadrupole rods in the ion deflector 32 can be supplied with suitable voltages from a power supply (which can be voltage source 42) to create a deflection field in the ion deflector quadrupole. Because of the configuration of the quadrupole rods and the applied voltages, the resulting deflection field can be effective at deflecting charged particles in the entering ion stream through an approximately 90 degree angle. The exit trajectory of the ion stream can thus be roughly orthogonal to the entrance trajectory (as well as to the longitudinal axis of the quadrupole).

As will be appreciated, the ion deflector 32 arranged in the shown quadrupole configuration can selectively deflect the various ion populations in the ion stream (both analyte and interferer type ions) through to the exit, while other neutrally charged, non-spectral interferences are discriminated against. Thus, the ion deflector 32 can selectively remove light photons, neutral particles (such as neutrons or other neutral atoms or molecules), as well as other gas molecules from the ion stream, which have little or no appreciable interaction with the deflection field formed in the quadrupole on account of their neutral change. The ion deflector 32 can be included in the mass spectrometer 10 as one possible means of eliminating non-spectral interferers from the ion stream, and in embodiments of the mass spectrometer 10 where no other means of achieving the same result may be convenient. As known by a person skilled in the art, there are other techniques to eliminate or reduce non-spectral interferers from the ion stream prior to introducing the ion beam into the cell.

The ion stream once exiting the ion deflector 32 along the exit trajectory can be transmitted to an entrance end of pressurized cell 36, and thereby admitted into the pressurized cell 36 through a suitable entrance member of the pressurized cell 36, such as entry lens 38, located at an entrance end of the pressurized cell 36. Accordingly, the entry lens 38 can provide an ion inlet for receiving the ion stream into the pressurized cell. If the ion deflector 32 is omitted from the mass spectrometer 10, the ion stream may be transmitted directly from either the skimmer 16 (or, if included, the secondary skimmer 18) to the entry lens 38. Downstream of the entry lens 38 at an exit end of the pressurized cell 36, a suitable exit member, such as exit lens 46, may also be provided. Exit lens 46 may provide an aperture through which ions traversing the pressurized cell 36 may be ejected to downstream mass analytical components of the mass spectrometer 10. The entry lens 38 can have a 4.2 mm entry lens orifice, as compared to a 3 mm exit lens orifice of the exit lens 46, though other size orifices may be viable as well to receive and eject the ion stream from the pressurized cell 36. Also, the pressurized cell 36 can be generally sealed off from the vacuum chamber 30 to define an interior space suitable for housing quantities of a collision (either reactive or inert) gas, as described in more detail below.

The pressurized cell 36 can be a quadrupole pressurized cell enclosing a quadrupole rod set 40 within its interior space. As is conventional, the quadrupole rod set 40 can comprise four cylindrical rods arranged evenly about a common longitudinal axis that is collinear with the path of the incoming ion stream. The quadrupole rod set 40 can be linked to voltage source 42, for example using power connection 44, to receive an RF voltage therefrom suitable for creating a quadrupolar field within the quadrupole rod set 40. As will be appreciated, the field formed in the quadrupolar rod set 40 can provide radial confinement for ions being transmitted along its length from the entrance end toward the exit end of the pressurized cell 36. As illustrated better in FIGS. 2A-2B, diagonally opposite rods in the quadrupole rod set 40 can be coupled together to receive out-of-phase RF voltages, respectively, from the voltage source 42. A dc bias voltage may also, in some instances, be provided to the quadrupole rod set 40. Voltage source 42 can also supply a cell offset (dc bias) voltage to the pressurized cell 36.

The quadrupole rod set 40 can moreover be aligned collinearly with the entry lens 38 and exit lens 46 along its longitudinal axis, thereby providing a complete transverse path through the pressurized cell 36 for ions in the ion stream. Thus, an entrance ellipse of the quadrupole rod set 40 can be aligned with the entry lens 38 to receive the incoming ion stream. The entry lens 38 may also be sized appropriately (e.g. 4.2 mm) to direct ion stream entirely, or at least substantially, within the entrance ellipse and to provide the ion stream having a selected maximum spatial width, for example but without limitation, in the range of 2 mm to 3 mm. Thus, the entry lens 38 can be sized so that most or all, but at a minimum a substantial part, of the ion stream is directed into the acceptance ellipse of the quadrupole rod set 40. The skimmers 16 and 18 may also be sized to affect the spatial width of the ion stream. In this way, the ion stream may be focused upstream of the quadrupole rod set 40 to reduce loss of ions and to provide efficient transmission through the quadrupole rod set 40.

A gas inlet 47 may also be included in the pressurized cell 36 providing fluid communication between a source of gas 48 and the interior space of pressurized cell 36. The source of gas 48 can be operable to inject a quantity of a selected gas into the pressurized cell 36 to collide with ions in the ion stream. The source of gas 48 may, according to embodiments of the invention, be selectable between a plurality of different types of gas. So for example, the source of gas 48 may provide a quantity of an inert gas within the pressurized cell 36 to a predetermined pressure, the gas being for example helium or neon. More generally, the inert gas can be any gas that is substantially inert toward both an analyte ion kind and an interferer ion kind in the ion stream. Moreover, assuming a first group of ions in the ion stream of a first polyatomic interfering kind, and a second group of ions in the ion stream of a second monatomic analyte kind, the chosen inert collision gas may collide with a substantially larger proportion of the first group of ions than with the second group of ions, to reduce the energies of the individual ions in the first group to a greater extent on average than the individual ions in the second group. Accordingly, the inert gas can be of a type that is suitable for operating the pressurized cell 36 for KED.

Moreover, the source of gas 48 may also provide the pressurized cell 36 with a quantity of a reactive gas selected from a plurality of different reactive gas types. The reactive gas can be selected, for example, to be reactive with an interferer ion kind, while at the same time being inert toward one or more analyte ion kinds. Alternatively, the selected reactive gas can be inert toward the interferer ion kind and reactive with one or more of the analyte ions. Embodiments of the invention may be directed to either scenario. For example, but without limitation, the source of gas 48 may provide the selected reactive gas within the pressurized cell 36 in the manner described in U.S. Pat. Nos. 6,140,638 and 6,627,912. Accordingly, if the reactive gas is selected to be reactive with the interferer ion kind, mass filtering may then be performed in the pressurized cell 36 to transmit only the analyte ion kind. Alternatively, the reactive gas may be selected to be reactive with a population of ions, other than a spectral interferer kind, in order to generate analyte product ions of interest. One type of reactive gas that can be selected is ammonia ($NH_3$). The reactive gas can also be provided within the pressurized cell 36 up to a predetermined pressure, which can be the same predetermined pressure as the inert gas, but can also be a different predetermined pressure. However, in some embodiments, both the inert and the reactive gas can be provided within the pressurized cell 36 to a predetermined pressure within the range of 1 millitorr to 40 millitorr.

A pump (not shown), which can be a mechanical pump like pumps 22, 26 and 34, can also be fluidly coupled to the pressurized cell 36 and can be operable to evacuate gas that is housed within the pressurized cell 36. Through synchronous operation of the pump and the source of gas 48, the pressurized cell 36 may be repeatedly and selectively filled with, and then emptied of, a suitable collision gas during operation of the mass spectrometer 10. For example, the pressurized cell 36 may be filled with and then emptied of a quantity of an inert gas, alternately with filling and emptying of a quantity of a selected reactive gas provided by the source of gas 48. In this way, the pressurized cell 36 may be made suitable for alternate and selective operation in the DRC and KED modes. As will be appreciated, however, and as described in more detail below, other parameters of other components of the mass spectrometer 10 may also be adjusted based on the mode of operation.

The ion optical elements located upstream of the quadrupole rod set 40 in the mass spectrometer 10 can also be configured so as to control each respective energy distribution, for example in terms of the corresponding range, of the various ion populations in the ion stream and to minimize energy separation during transmission from the ion source 12 to the quadrupole rod set 40. One aspect of this control can involve maintain the entry lens 38 at or slightly less than ground potential, thereby minimizing any ion field interactions at the entry lens 38 that could otherwise cause energy separation in the ion populations. For example, the entry lens 38 can be supplied by the power supply 42 with an entrance potential falling in the range between −5V and +2V. Alternatively, the entry potential supplied to the entry lens 38 can be in the range between −3V and 0 (ground potential). Maintaining the magnitude of the entry potential at a relatively low level can help to keep the corresponding energy distributions of different ion groups in the ion stream within a relatively small range.

In some embodiments, the range of the corresponding energy distribution for each respective ion population in the ion stream can be controlled and maintained, during transmission from the ICP ion source 20 to the pressurized cell 36, to be within 5 percent of the corresponding initial range. Alternatively, each ion population's respective energy distribution can be controlled and maintained to within a maximum range selected to provide good kinetic energy discrimination in the pressurized cell 36 through collision with the inert gas therein. This maximum range of the corresponding energy distributions can be equal to about 2 eV, measured at full-width, half-max.

The exit lens 46 can also be supplied with a dc voltage by the voltage source 42 so as to be maintained at a selected exit potential. In some embodiments, the exit lens 46 can receive a lower (i.e. more negative) exit potential than the entrance potential provided to the entry lens 38, to attract positively charged ions in the pressurized cell 36 toward to the exit end of the pressurized cell 36. Moreover, the absolute magnitude of the exit potential can be larger, perhaps even significantly larger, than the supplied entrance potential. The exit potential at which the exit lens 46 can be maintained may, in some embodiments, be within the range defined between −40V and −18V. The exit potential may more particularly be somewhere within the range −35V to −25V. It should be appreciated that it is not strictly necessary for the exit lens 46 and entry lens 38 to be supplied by the same voltage source, in this case voltage source 42. One or more different voltage sources may be linked to these components (or any other components in the system 10) to provide voltages.

Mass analyzer 50 is located downstream of the pressurized cell 36 with, optionally, pre-filter stubby rods 52 interposed therebetween. Mass analyzer 50 can generally be any type of suitable mass analyzer including, but without limitation, a resolving quadrupole mass analyzer, a hexapole mass analyzer, a time-of-flight (TOF) mass analyzer, a linear ion trap analyzer, or some combination of these elements. As shown in FIG. 1, mass analyzer 50 comprises a quadrupole and can be configured for Mass-Selective Axial Ejection (MSAE) as described in U.S. Pat. No. 6,177,668, the entire contents of which are herein incorporated by reference. Accordingly, voltage source 56 can be linked to the downstream mass analyzer 50 to supply suitable RF/DC voltages and, optionally, an auxiliary voltage for use in MSAE as described in U.S. Pat. No. 6,177,668. Ions received into the mass analyzer 50 can be mass differentiated (in the case of MSAE, in space, not time) and transmitted to the detector 54 for detection, which can be any suitable detector as will be understood. Voltage source 56 can also supply a downstream offset (dc) bias voltage to the mass analyzer 50. The mass analyzer 50 can be housed in a vacuum chamber evacuated by the mechanical pump 58.

Pre-filter 52 can be interposed between the pressurized cell 36 and the downstream mass analyzer 50 for use as a transfer element between these two components. Accordingly, pre-filter 52 can be operated in RF-only mode to provide radial confinement of the ion stream between the pressurized cell 36 and the downstream mass analyzer 50 and to reduce the effects of field-fringing that might otherwise occur. In other embodiments, pre-filter 52 may also receive a dc voltage to provide additional mass filtering of ions before transmission into the quadrupole analyzer 50, for example to address space charge issues, or the like.

As described herein above, the pressurized cell 36 can be supplied with a cell offset voltage and the mass analyzer 50 can be supplied with a downstream offset voltage, which can be dc voltages supplied by a single or multiple different voltage sources linked to the corresponding component. The amplitude of each applied offset voltage can be fully controllable. Indirectly, therefore, or perhaps directly, the difference between the cell offset and downstream voltages can also be controlled.

In one case, the downstream offset voltage can be more positive than the cell offset voltage, thereby maintaining the mass analyzer 50 at an electrical potential above the pressurized cell 36. For positive ions transmitting from the pressurized cell 36 to the mass analyzer 50, this potential difference can present a positive potential barrier for ions to overcome. In other words, the relative positive difference can create an exit barrier at the downstream end of the pressurized cell 36 for ions to penetrate. Therefore, ions with at least a certain minimum kinetic energy can penetrate the exit barrier, while slower ions not having sufficient kinetic energy can be trapped within the pressurized cell 36. If the strength of the exit barrier is selected appropriately, for example through control of the size of the potential difference between the mass analyzer 50 and the pressurized cell 36, then the exit barrier can discriminate selectively against one population or group of ions relative to another, such that a greater proportion of the one group of ions relative to the other may be trapped by the barrier and prevented from exiting the pressurized cell 36. Controlling the downstream offset voltage to be more positive than the cell offset voltage can make the mass spectrometer 10 suitable for KED operation.

In another case, however, the downstream and cell offset voltages (and thus also the difference therebetween) can be controlled to make the cell offset voltage more positive than the downstream offset voltage. With the offset voltages thus controlled, the mass spectrometer 10 can be suitable for DRC operation. Rather than providing an exit barrier as in the above described case, maintaining the mass analyzer 50 at a lower electrical potential than the pressurized cell 36 can accelerate ions into the mass analyzer 50 from the pressurized cell 36 and provide more efficient transmission of analyte ions between these two stages. As noted above, the interferer ions can react with the reactive gas to form product ions, which can then be destabilized and ejected by tuning the pressurized cell 36 to apply a narrow bandpass filter around the m/z of the analyte ions. This way only the analyte ions can be accelerated into the mass analyzer 50. If a trapping element is provided downstream of the pressurized cell 36, the accelerating force provided by the potential drop can also sometimes be an effective way to induce in-trap ion fragmentation of the analyte ions, for example, if fragmentation is wanted.

Mode controller 60 can control and coordinate operation of the mass spectrometer 10 for dual KED/DRC operation. For this purpose, mode controller 60 can be linked to each of the gas source 48, the pump, the voltage source 42 for the pressurized cell 36, and the voltage source 56 for the downstream mass analyzer 50, as well as any other voltage or gas sources included in the mass spectrometer 10 not shown in FIG. 1. Accordingly, mode controller 60 can be operable to switch the mass spectrometer 10 from the KED to the DRC mode of operation, and further from the DRC back to the KED mode of operation. More generally, the mode controller 60 can selectably switch between these two modes of operation. As will be described in more detail, in order to make the switch from one mode of operation to the other, the mode controller 60 can set, adjust, reset, or otherwise control, as needed, one or more settings or parameters of the mass spectrometer system 10 based one or more other setting or parameters.

The mode controller 60 can comprise both hardware or software components, including a processor and memory linked to the processor. As is known, the processor can be provided in the form of a central processing unit (CPU), a microcontroller or microprocessor, a general purpose computer, an application specific processing unit, and the like. The memory can comprise both volatile and non-volatile storage media on which executable instructions for the processor, as well as other system data, can be stored in non-transitory form. The mode controller 60 can also comprise a database of information about atoms, molecules, ions, and the like, which can include the m/z ratios of these different compounds, ionization energies, and other common information. The database can include further data relating to the reactivity of the different compounds with other compounds, such as whether or not two compounds will form molecules or otherwise be inert toward each other. The instructions stored in the memory can execute a software module or control routine for the mass spectrometer 10, which in effect can provide a controllable model of the system. As will be described in more detail below, the mode controller 60 can use information accessed from the database together with one or software modules executed in the processor to determine control parameters or values for different modes of operation for the mass spectrometer 10, including the KED and DRC modes of operation. Using input interfaces to receive control instructions and output interfaces linked to different system components in the mass spectrometer 10, the mode controller can perform active control over the system.

In the KED mode of operation, the mode controller 60 can enable a source of the inert gas in the gas source 48, such as helium, and then drive the gas source 48 to fill the pressurized cell 36 with a quantity of the inert gas up to predetermined pressure. The mode controller 60 can also set the downstream offset voltage to be more positive than the cell offset voltage, thereby forming the exit barrier at the exit end of the pressurized cell 36. For example, the mode controller 60 can control the downstream voltage to be between 2V and 5V more positive than the cell offset voltage when operating in the KED mode.

Ions admitted into the pressurized cell 36 be collide with the inert collision gas and undergo reductions in their respective kinetic energies. The average reduction in kinetic energy can depend on the average collisional cross-section of the ion kind, with ions of a larger collisional cross-section tending to undergo greater reductions in kinetic energy, relative to ions with a smaller cross-section, even where the two kinds of ions have substantially the same or similar m/z ratios. Thus, due to collisions with the inert gas, a group of polyatomic interferer ions can have its average kinetic energy reduced to a greater extent than a group of monatomic analyte ions. If the corresponding energy distributions of these two groups of ions are controlled during transmission, from the ion source 12 to the pressurized cell 36, to be within the selected maximum range for the mass spectrometer 10, then collision with the inert gas can introduce an energy separation between the two groups. Thus, a larger proportion of the interferer ion group can experience reduced energies relative to the analyte ion group with the effect that, through mode controller 60 controlling the size of the exit barrier, a greater proportion of the interferer ions will be unable to penetrate the exit barrier than the analyte ions.

The required amplitude of the exit barrier can generally depend on the interferer and analyte ion kinds, and therefore the mode controller 60 may control the difference between the downstream and cell offset voltages based on one or both of the interferer and analyte ion kinds. For example, mode controller 60 can determine a voltage difference in the above listed range of 2V to 5V based upon the interferer and/or analyte ion kinds. Additionally, the mode controller 60 may control the difference based upon other system parameters, such as the entry or exit potentials applied to the entry lens 38 and the exit lens 46, respectively. The mode controller 60 can also be configured to adjust or tune the downstream and cell offset voltages forming the exit barrier to improve kinetic energy discrimination between the interferer and analyte ions. Moreover, the mode controller 60 can also be configured to adjust the entrance potential applied to the entry lens 38 in order to control the range of energy distributions of the constituent ion populations entering into the pressurized cell 36. The mode controller 60 may also control the RF voltage supplied to the quadrupole rod set 40 by the voltage source 42 in order to set or adjust the strength of the quadrupolar confinement field. In this way, the mode controller 60 can set the quadrupolar confinement field within the quadrupole rod set 40 to strength sufficient to confine at least a substantial portion of analyte ions within the quadrupole rod set 40 when scattered due to collision with the inert gas. Any of the above determinations by the mode controller 60 may be based upon interferer and/or analyte ion kind.

In order to switch from the KED mode to the DRC mode of operation, mode controller 60 can instruct the pump to evacuate the inert gas from the pressurized cell 36 and can enable a selected reactive gas in the gas source 48 to be pumped into the pressurized cell 36 to a predetermined pressure, for example. The reactive gas selected can be one that is substantially inert toward the analyte ions but reactive with the interferer ions (or vice versa). The mode controller 60 can also, for example by accessing a linked database, determine one or more types of potential interferer ions based upon one or more identified analyte ions of interest. The interferer ion kinds determined by the mode controller 60 may have substantially the same or similar m/z ratios as the analyte ion kinds. The mode controller 60 can also select a suitable reactive gas in a similar way. Once a suitable reactive gas has been selected and enabled in the gas source 48, mode controller can control the gas source 48 to inject a quantity of the reactive gas into the pressurized cell 36.

For operation in the DRC mode, the mode controller 60 may control operation of the mass spectrometer 10 substantially as described in U.S. Pat. Nos. 6,140,638 and 6,627,912. Additionally, the mode controller 60 can be configured to instruct the voltage source 42 to supply a downstream offset voltage that is more negative than the cell offset voltage. The difference between these two voltages may be controlled by the mode controller 60, for example, to lie within the range between 4V and 6V, so that the mass analyzer 50 is at an electrical potential that is between 4V and 6V more negative than the pressurized cell 36. The determination of the difference may again be made based upon the interferer and/or analyte ion kinds. The mode controller 60 may also be configured to adjust or tune the offset voltage difference.

In order to switch from the DRC mode of operation back to the KED mode of operation, the mode controller 60 can instruct the pump to evacuate the selected reactive gas from the pressurized cell, and subsequently control the gas source 48 to provide a quantity of the inert gas within the pressurized cell. The downstream and cell offset voltages, as well as other system parameters, may also be adjusted by the mode controller 60 as described above to be suitable for KED operation.

Figure 2B:
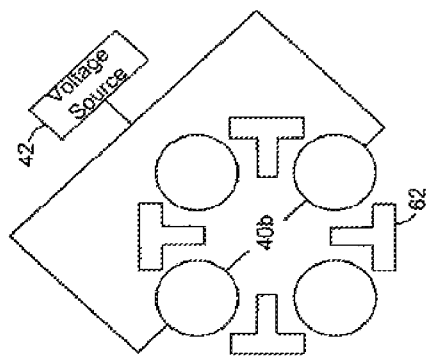
Figure 2A:
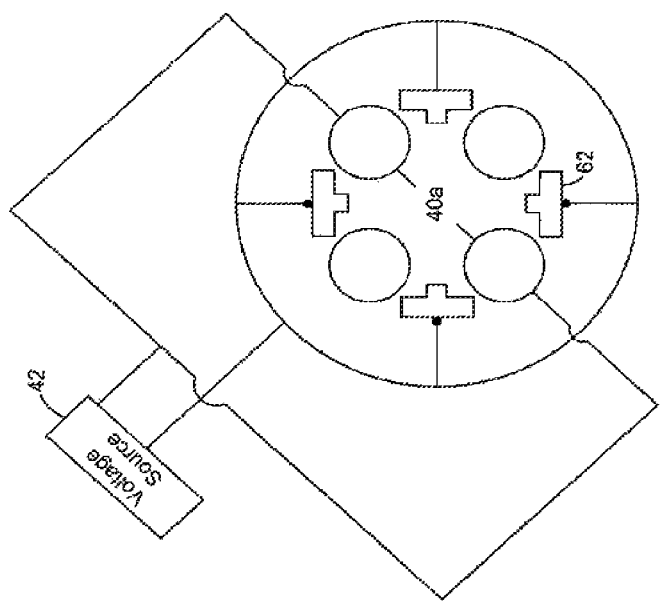
FIG. 2a, in front cross-sectional view, illustrates a set of auxiliary electrodes that can be included in the mass spectrometer system shown in FIG. 1, in alternative embodiments of the present invention.

With reference now to FIGS. 2A-2B, illustrated therein, in front and rear cross-sectionals views, respectively, are auxiliary electrodes 62 that can be included in alternative embodiments of the present invention. These figures illustrate quadrupole rod set 40 and voltage source 42, as well as the connections therebetween. The pair of rods 40a can be coupled together (FIG. 2a) as can the pair of rods 40b (FIG. 2b) to provide the quadrupolar confinement field. For example, the pair of rods 40a can be supplied with a voltage equal to $V_o + A \cos \omega t$, where A is the amplitude of the supplied RF and $V_o$ is a dc bias voltage. For quadupolar operation, the pair of rods 40b can then be supplied with a voltage equal to $-V_o - A \cos \omega t$.

The auxiliary electrodes 62 can be included in the pressurized cell 36 to supplement the quadrupolar confinement field with an axial field, i.e. a field that has a dependence on axial position within the quadrupole rod set. As illustrated in FIGS. 2A-2B, the auxiliary electrodes can have a generally T-shaped cross-section, comprising a top portion and a stern portion that extends radially inwardly toward the longitudinal axis of quadruple rod set. The radial depth of the stem blade section can vary along the longitudinal axis to provide a tapered profile along the length of the auxiliary electrodes 62. FIG. 2A shows the auxiliary electrodes from the downstream end of the pressurized cell 36 looking upstream toward the entrance end, and FIG. 2B shows the reverse perspective looking from the entrance end downstream to the exit end. Thus, the inward radial extension of the stem portions lessens moving downstream along the auxiliary electrodes 62.

Each individual electrode can be coupled together to the voltage source 42 to receive a dc voltage. As will be appreciated, this geometry of the auxiliary electrodes 62 and the application of a positive dc voltage can create an axial field of a polarity that will push positively charged ions toward the exit end of the pressurized cell 36. It should also be appreciated that other geometries for the auxiliary electrodes could be used to equal effect, including, but not limited to, segmented auxiliary electrodes, divergent rods, inclined rods, as well as other geometries of tapered rods and reduced length rods. Neglecting fringe effects at the ends of the rods and other practical limitations, the axial field created by the auxiliary electrodes can have a substantially linear profile. The gradient of the linear field can also be controllable based upon the applied dc voltage and the electrode configuration. For example, the applied dc voltage can be controlled to provide an axial field gradient in the range between 0.1 V/cm and 0.5 V/cm. In some embodiments, the axial field gradient can be controlled so that the axial field gradient is in the range between 0.15 V/cm and 0.25 V/cm. For a given electrode geometry, it will be well understood how to determine a required dc voltage to achieve a desired axial field gradient. But for example, without limitation, dc voltages in the range 0 to 475 V.

The mode controller 60 can also control the voltage source 42 so that the supplied dc voltage to the auxiliary electrodes 62 forms an axial field of a selected field strength, defined for example in terms of its axial gradient. The auxiliary electrodes 62 may be energized for each of the KED and DRC modes of operation, though at different field strengths. Mode controller 60 may control the relative field strengths for each mode of operation. In either mode of operation, the auxiliary electrodes 62 can be effective in sweeping reduced energy ions out of quadrupole by pushing the ions toward the exit end of the pressurized cell 36. The magnitude of the applied axial field strength can be determined by the mode controller 60 based upon the interferer and analyte ion kinds in the ion stream, as well as other system parameters as described herein.

While the above description provides examples and specific details of various embodiments, it will be appreciated that some features and/or functions of the described embodiments admit to modification without departing from the scope of the described embodiments. The above description is intended to be illustrative of the invention, the scope of which is limited only by the language of the claims appended hereto.

The invention claimed is:

1. A system comprising:
an ion source;
a cell coupled to the ion source and configured to operate in at least three different modes comprising a collision mode, a reaction mode and a standard mode, the three different modes each configured to select analyte ions from a plurality of ions introduced into the cell from the ion source, the cell configured to couple to the ion source at an entrance aperture to permit introduction of the plurality of ions from the ion source into the cell, the cell further comprising a gas inlet configured to receive a substantially inert gas to pressurize the cell in a collision mode and to receive a reactive gas to pressurize the cell in a reaction mode, the pressurized cell further comprising an exit aperture configured to provide the analyte ions from the cell;
a mass analyzer coupled to the cell; and
a controller electrically coupled to the cell and configured to provide the substantially inert gas to pressurize the cell in the collision mode, configured to provide the reactive gas to pressurize the cell in the reaction mode, and configured to maintain the cell under vacuum in the standard mode, in which the controller is configured to provide an effective voltage from a voltage source to the cell in the collision mode to select ions comprising an energy greater than a barrier energy and an effective voltage from the voltage source in the reaction mode to select ions using mass filtering.

2. The system of claim 1, in which the pressurized cell comprises a quadrupole.

3. The system of claim 2, in which the voltage is provided to the quadrupole to provide a quadrupolar field effective to confine a substantial amount of non-analyte ions in the plurality of introduced ions by colliding the non-analyte ions with the substantially inert gas in the collision mode.

4. The system of claim 3, further comprising axial electrodes configured to provide an axial field to direct the analyte ions from the entrance aperture toward an exit aperture of the pressurized cell.

5. The system of claim 4, in which the axial field strength has an axial field gradient between 0.1 V/cm and 0.5 V/cm.

6. The system of claim 2, further comprising an exit member proximal to an exit aperture of the pressurized cell, the exit member comprising an exit potential to attract analyte ions toward the exit aperture of the pressurized cell.

7. The system of claim 6, in which the exit potential is between about −60 Volts and −18 Volts in the collision mode.

8. The system of claim 6, in which the exit potential is between about −20 Volts and 0 Volts in the reaction mode.

9. The system of claim 6, further comprising an entrance member proximal to the entrance aperture of the pressurized cell, the entrance member comprising an entrance potential more positive than the exit potential in the collision mode.

10. The system of claim 9, in which the entrance potential is between −10 Volts and +2 Volts.

11. The system of claim 6, further comprising an entrance member proximal to the entrance aperture of the pressurized cell, the entrance member comprising an entrance potential substantially the same as the exit potential in the reaction mode.

12. The system of claim 11, in which the exit member comprises a potential between −60 Volts and −18 Volts in the collision mode.

13. The system of claim 11, in which the exit member comprises a potential between −20 Volts and 0 Volts in the reaction mode.

14. The system of claim 1, in which the mass analyzer is positioned between the ion source and the cell.

15. The system of claim 1, in which the mass analyzer is positioned downstream from the cell.

16. The system of claim 1, further comprising a detector coupled to the cell.

17. The system of claim 1, in which the ion source is configured as an inductively coupled plasma.

18. The system of claim 1, further comprising an additional cell coupled to the cell, the additional cell configured to operate in at least three different modes comprising a collision mode, a reaction mode and a standard mode.

19. The system of claim 18, in which the additional cell is configured to operate in a standard mode when the cell is being operated in the collision gas mode or the reaction mode.

* * * * *